(12) United States Patent
Shimizu

(10) Patent No.: US 6,654,123 B2
(45) Date of Patent: Nov. 25, 2003

(54) SENSOR UTILIZING ATTENUATED TOTAL REFLECTION

(75) Inventor: Hitoshi Shimizu, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 27 days.

(21) Appl. No.: 10/026,960

(22) Filed: Dec. 27, 2001

(65) Prior Publication Data

US 2002/0093659 A1 Jul. 18, 2002

(30) Foreign Application Priority Data

Dec. 27, 2000 (JP) ........................................ 2000-398310

(51) Int. Cl.7 .............................................. G01N 21/55
(52) U.S. Cl. ....................................................... 356/445
(58) Field of Search ................................. 356/445–448; 250/227.14, 227.25, 227.24, 216

(56) References Cited

U.S. PATENT DOCUMENTS

| | | | |
|---|---|---|---|
| 4,844,613 A | | 7/1989 | Batchelder et al. |
| 5,351,127 A | * | 9/1994 | King et al. ................. 356/445 |
| 5,485,277 A | | 1/1996 | Foster |
| 5,912,456 A | | 6/1999 | Melendez et al. |
| 5,923,031 A | * | 7/1999 | Naya ..................... 250/227.25 |
| 5,991,048 A | * | 11/1999 | Karlson et al. ............. 356/445 |

FOREIGN PATENT DOCUMENTS

| | | |
|---|---|---|
| JP | 6-167443 | 6/1994 |
| JP | 6167443 A | 6/1994 |
| JP | 10-239233 | 9/1998 |
| JP | 11326194 A | 11/1999 |
| JP | 11-326194 | 11/1999 |

OTHER PUBLICATIONS

Surface Refracto–Sensor Using Evanescent Waves Principles and Instrumentations, Takayuki Okamoto, Optical Engineering Laboratory The Institute of Physical and Chemical Research (RIKEN) (Received Dec. 8, 1997), "Spectral Researches" vol. 47, No. 1, 1998.

* cited by examiner

Primary Examiner—Michael P. Stafira
(74) Attorney, Agent, or Firm—Sughrue Mion, PLLC

(57) ABSTRACT

A sensor utilizing attenuated total reflection (ATR) is provided with a dielectric block, a thin film layer formed on a surface thereof, a light source for emitting a beam, and an optical system for making the beam enter the dielectric block at various angles of incidence so that a condition for total internal reflection is satisfied at an interface between the dielectric block and the thin film layer. The sensor is further provided with a photodetection section for detecting the ATR, a differentiation section for differentiating signals output from the light-receiving elements of the photodetection section, in a direction in which the light-receiving elements are juxtaposed, and an adjustment section for optically expanding the width of a dark line, corresponding to the ATR, of the beam which falls on the photodetection section, so that the width of the dark line becomes greater than a pitch between the light-receiving elements.

23 Claims, 8 Drawing Sheets

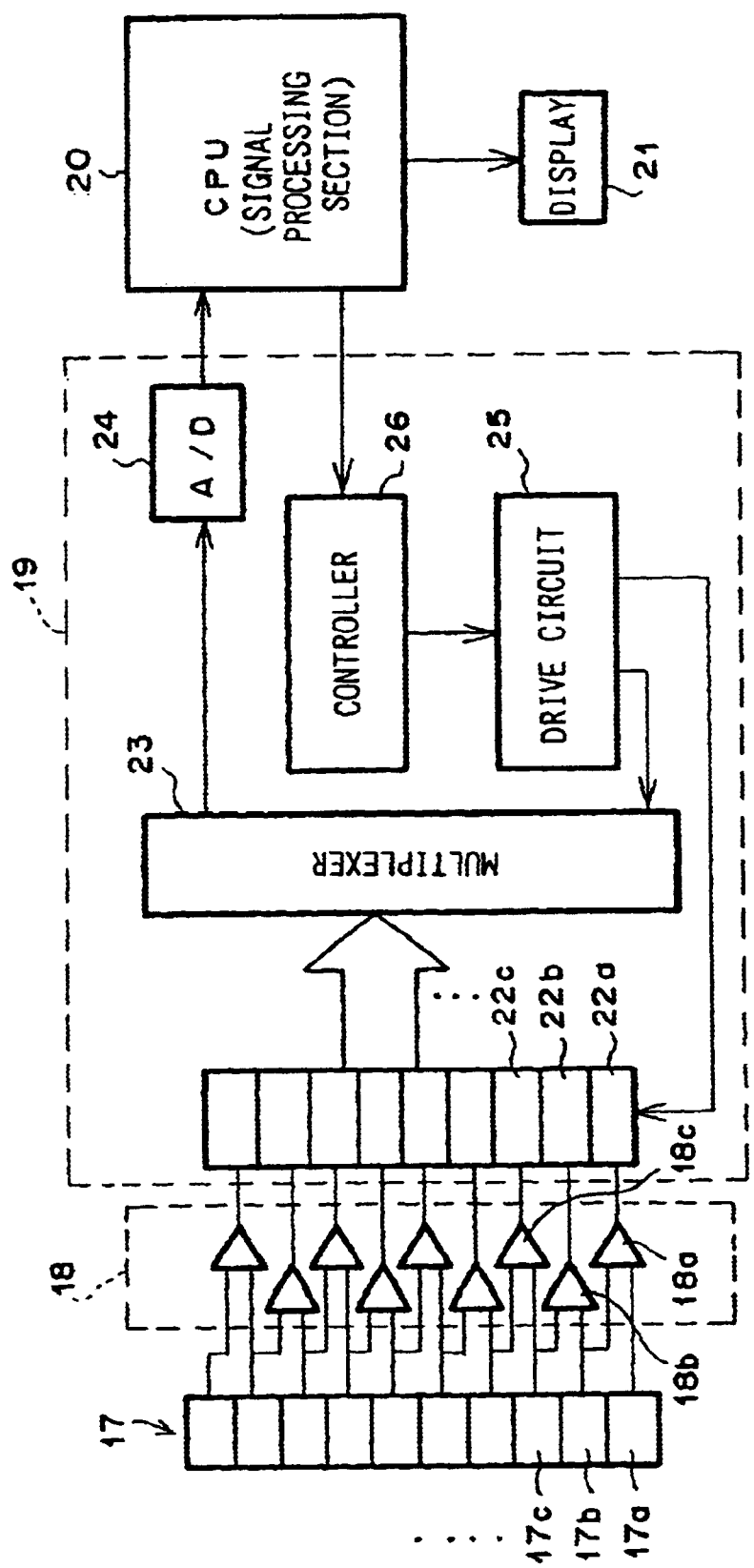

F I G. 3A
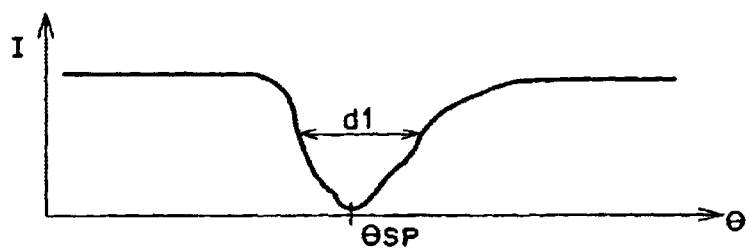
F I G. 3B
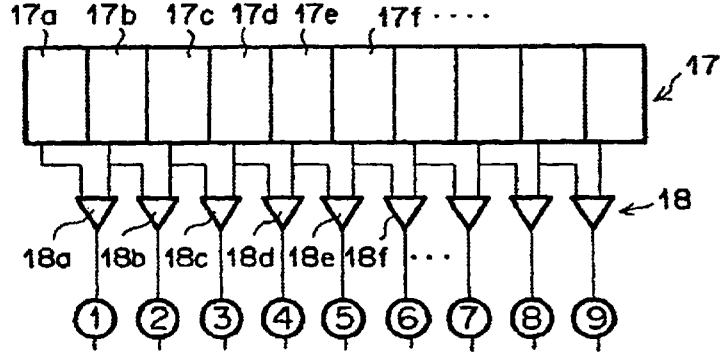
F I G. 3C
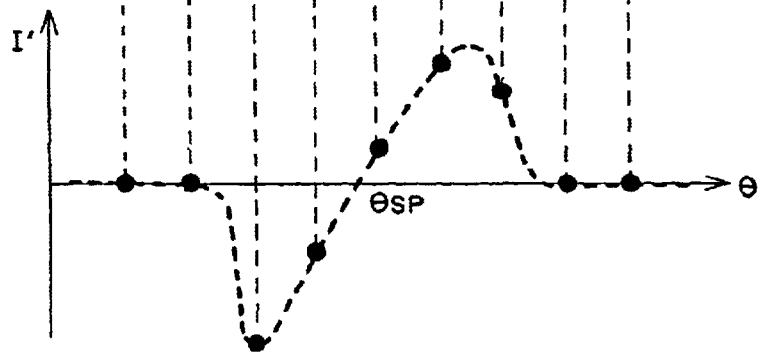

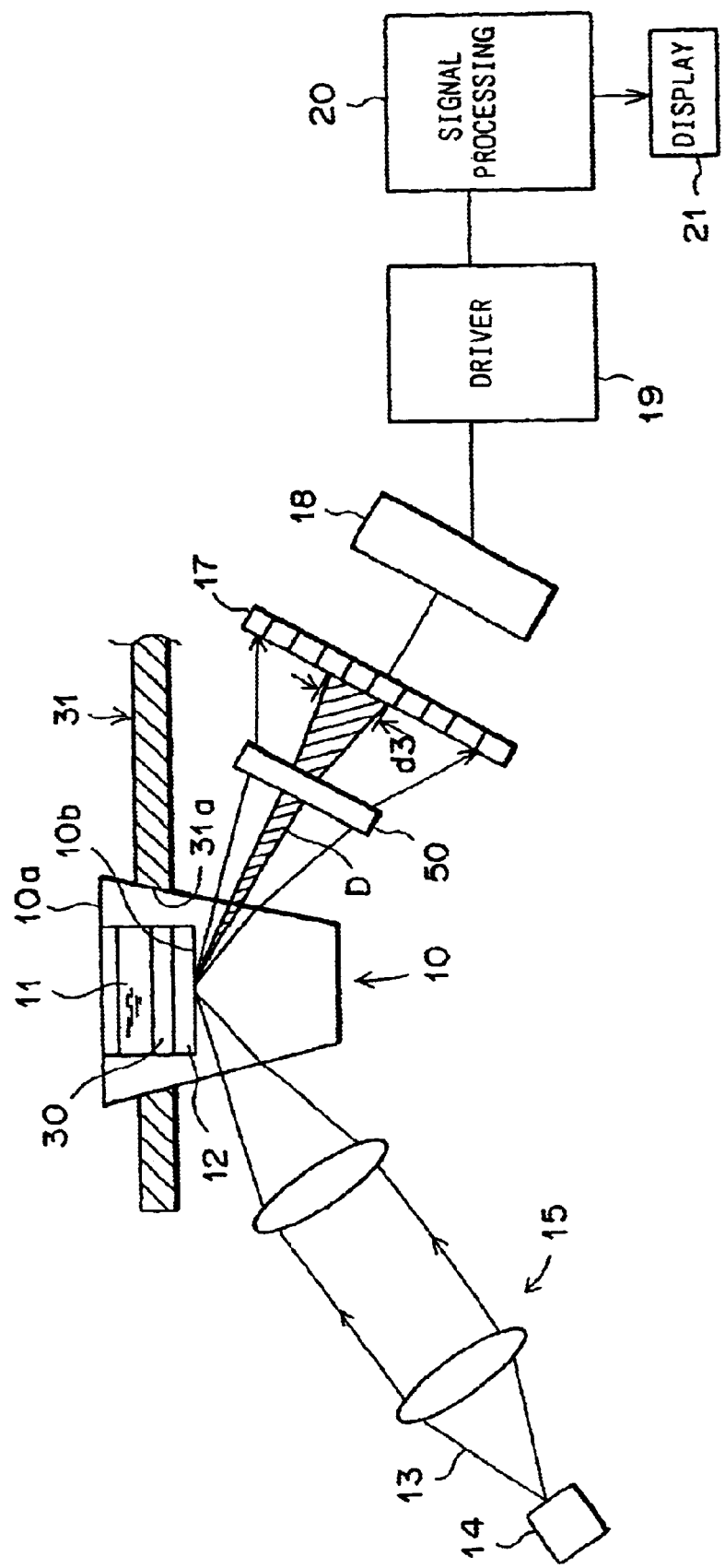

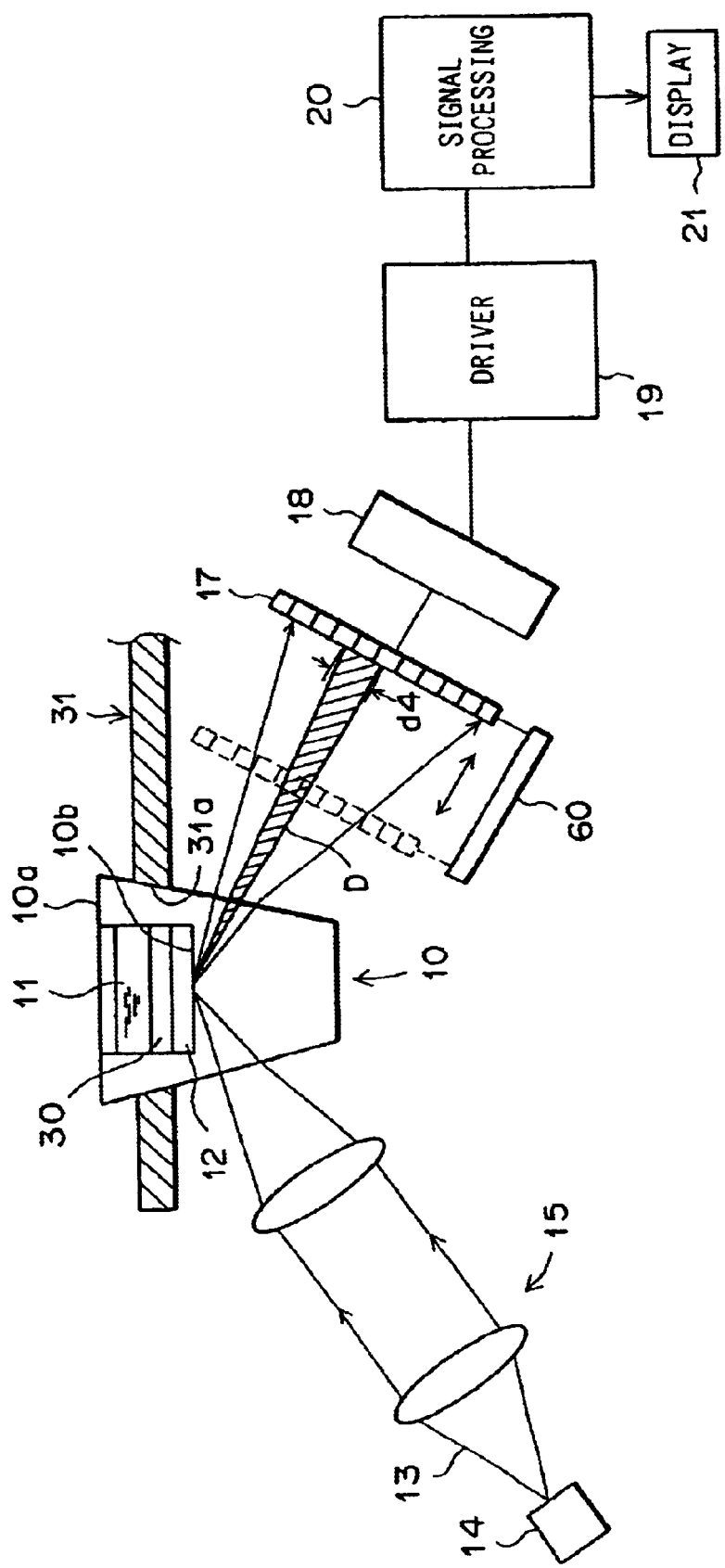

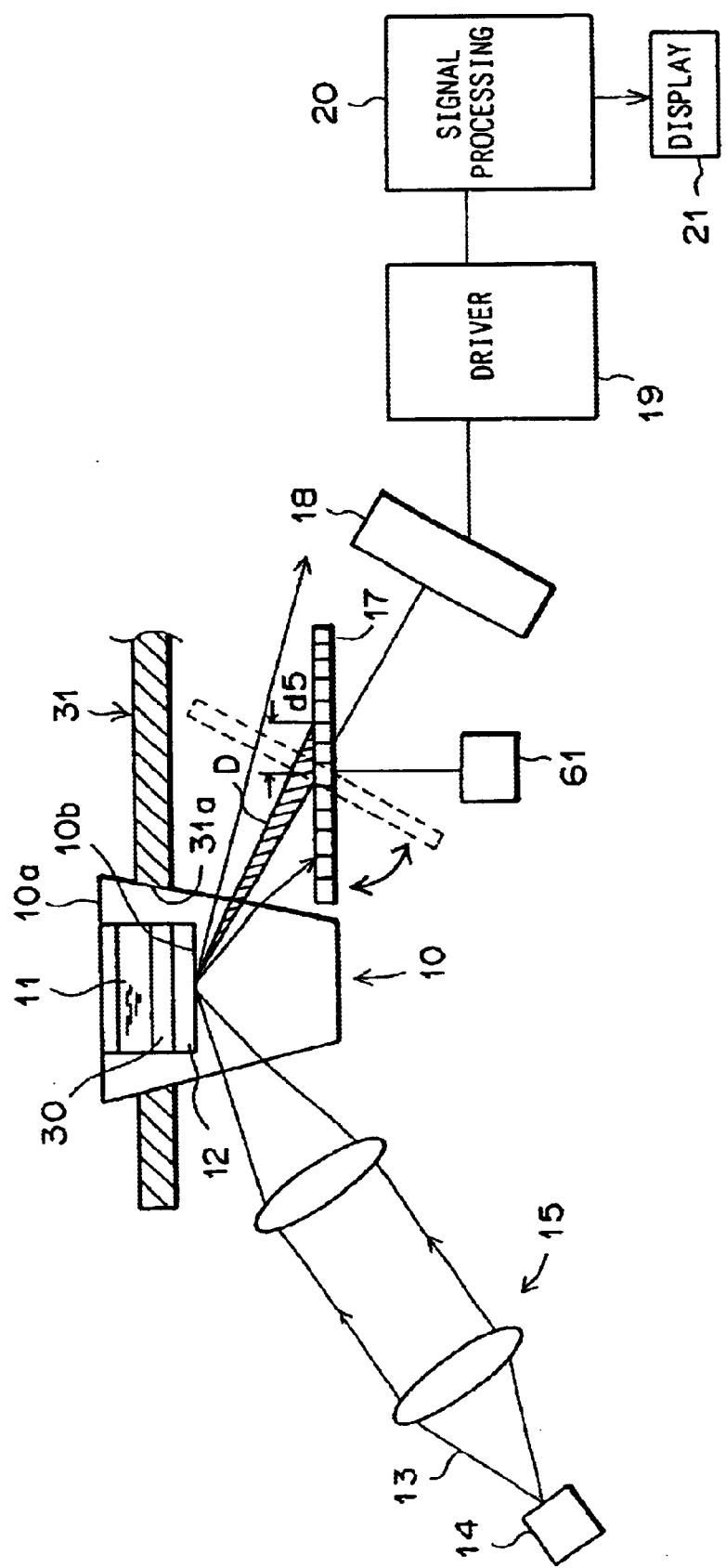

SENSOR UTILIZING ATTENUATED TOTAL REFLECTION

BACKGROUND OF THE INVENTION

1. Field of the Invention

The present invention relates to a sensor utilizing attenuated total reflection (hereinafter referred to as ATR), such as a surface plasmon resonance sensor for quantitatively analyzing a substance in a sample by utilizing excitation of a surface plasmon, and more particularly to a sensor, utilizing ATR, of a type that detects a dark line occurring in a reflected light beam due to ATR by the use of photodetection means consisting of a plurality of light-receiving elements juxtaposed in a predetermined direction.

2. Description of the Related Art

In metals, if free electrons are caused to vibrate in a group, compression waves called plasma waves will be generated. The compression waves generated in a metal surface are quantized and called a surface plasmon.

A variety of surface plasmon resonance sensors have been proposed for quantitatively analyzing a substance in a sample by taking advantage of a phenomenon that a surface plasmon is exited by light waves. Among such sensors, one employing a system called "Kretschmann configuration" is particularly well known (e.g., see Japanese Unexamined Patent Publication No. 6(1994)-167443).

The surface plasmon resonance sensor employing the "Kretschmann configuration" is equipped mainly with a dielectric block formed, for example, into the shape of a prism; a metal film, formed on a surface of the dielectric block, for placing a sample thereon; a light source for emitting a light beam; an optical system for making the light beam enter the dielectric block at various angles of incidence so that the condition for total internal reflection is satisfied at the interface between the dielectric block and the metal film; and photodetection means for detecting the state of the surface plasmon resonance, that is, the state of ATR by measuring the intensity of the light beam satisfying total internal reflection at the interface.

In order to obtain various angles of incidence, as described above, a relatively thin light beam may be caused to strike the above-mentioned interface at different angles of incidence, or relatively thick convergent or divergent rays may be caused to strike the interface so that they contain components incident at various angles. In the former, the light beam whose reflection angle varies with a change in the incidence angle of the incident light beam can be detected by a small photodetector that is moved in synchronization with the variation in the reflection angle, or by an area sensor extending in the direction in which the angle of reflection varies. In the latter, on the other hand, rays reflected at various angles can be detected by an area sensor extending in the direction in which all of the reflected rays can be received.

In the surface plasmon resonance sensor mentioned above, where $K_{sp}$ represents the wave number of the surface plasmon, $\omega$ represents the angular frequency of the surface plasmon, c represents the speed of light in vacuum, and $\epsilon_m$ and $\epsilon_s$ represent the dielectric constants of the metal and the sample, respectively.

If the dielectric constant $\epsilon_s$ of the sample is found, the density of a specific substance in the sample is found based on a predetermined calibration curve, etc. As a result, by finding the incidence angle $\theta_{sp}$ at which the intensity of reflected light drops, the dielectric constant of the sample, that is, the properties of the sample related to the refractive index thereof can be specified.

In this kind of surface plasmon resonance sensor, photodetection means in the form of an array can be employed with the object of measuring the aforementioned incidence angle $\theta_{sp}$ with a high degree of accuracy and in a large dynamic range, as disclosed in Japanese Unexamined Patent Publication No. 11(1999)-326194. The photodetection means is formed by a plurality of light-receiving elements juxtaposed in a predetermined direction. The light-receiving elements are disposed to respectively receive the components of a light beam satisfying total internal reflection at various angles of reflection at the aforementioned interface.

In that case, differentiation means is provided for differentiating the photodetection signals output by the light-receiving elements of the aforementioned photodetection if a light beam strikes the metal film at a specific incidence angle $\theta_{sp}$ equal to or greater than a critical angle of incidence at which total internal reflection takes place, evanescent waves having electric field distribution are generated in the sample in contact with the metal film, whereby a surface plasmon is excited at the interface between the metal film and the sample. When the wave vector of the evanescent light is equal to the wave number of the surface plasmon and therefore the wave numbers between the two are matched, the evanescent waves and the surface plasmon resonate and light energy is transferred to the surface plasmon, whereby the intensity of light satisfying total internal reflection at the interface between the dielectric block and the metal film drops sharply. The sharp intensity drop is generally detected as a dark line by the above-mentioned photodetection means.

Note that the above-mentioned resonance occurs only when the incident light beam is a p-polarized light beam. Therefore, in order to make the resonance occur, it is necessary that a light beam be p-polarized before it strikes the interface.

If the wave number of the surface plasmon is found from a specific incidence angle $\theta_{sp}$ at which ATR takes place, the dielectric constant of a sample can be obtained by the following Equation:

$$K_{sp}(\omega)=(\omega/c)\{\epsilon_m(\omega)\epsilon_s\}^{1/2}/\{\epsilon_m(\omega)+\epsilon_s\}^{1/2}$$

means, in the direction in which the light-receiving elements are juxtaposed. The properties of the sample related to the refractive index thereof are often analyzed based on differentiated values output by the differentiation means, particularly the differentiated value corresponding to a dark line that occurs in a reflected light beam.

In addition, a leaky mode sensor is known as a similar sensor making use of ATR, as disclosed, for instance, in "Spectral Researches," Vol. 47, No.1 (1998), pp. 21 to 23 and pp. 26 and 27. The leaky mode sensor is constructed mainly of a dielectric block in the form of a prism, for example; a cladding layer formed on a surface of the dielectric block; an optical waveguide layer, formed on the cladding layer, for placing a sample thereon; a light source for emitting a light beam; an optical system for making the light beam enter the dielectric block at various angles of incidence so that the condition for total internal reflection is satisfied at the interface between the dielectric block and the cladding layer; and photodetection means for detecting the excited state of the waveguide mode, that is, the state of ATR by measuring the intensity of the light beam satisfying total internal reflection at the interface between the dielectric block and the cladding layer.

In the leaky mode sensor with the construction mentioned above, if a light beam falls on the cladding layer through the dielectric block at angles of incidence equal to or greater than an angle of incidence at which total internal reflection takes place, the light beam is transmitted through the cladding layer and then only light with a specific wave number, incident at a specific angle, is propagated in the optical waveguide layer in a waveguide mode. If the waveguide mode is excited in this manner, the greater part of the incident light is confined within the optical waveguide layer, and consequently, ATR occurs in which the intensity of light satisfying total internal reflection at the above-mentioned interface drops sharply. Since the wave number of light propagating in the optical waveguide layer depends on the refractive index of the sample on the optical waveguide layer, the refractive index of the sample and/or the properties of the sample related to the refractive index thereof can be analyzed by finding the above-mentioned specific angle of incidence at which ATR takes place.

The leaky mode sensor also can employ the aforementioned photodetection means in the form of an array in order to detect the position of a dark line occurring in the reflected light by ATR. In addition, the aforementioned differentiation means is often employed along with the photodetection means.

In the field of pharmaceutical research, etc., the above-mentioned surface plasmon resonance sensor and leaky mode sensor are sometimes used in a random screening method of finding a specific substance that couples with a desired sensing medium. In this case, a sensing medium is placed on the aforementioned thin film layer (i.e., the metal film in the case of the surface plasmon resonance sensor, or the cladding layer and the optical waveguide layer in the case of the leaky mode sensor), and various solutions of substances (liquid sample) are added to the sensing medium, and each time a predetermined time elapses, the aforementioned differentiated value is measured. If the added substances are coupled with the sensing medium, the refractive index of the sensing medium varies with the lapse of time by the coupling. Therefore, by detecting the above-mentioned differentiated value every time a predetermined time elapses and then judging whether or not the differentiated value has been varied, it can be judged whether or not the added substances and the sensing medium have been coupled, that is, whether or not the added substances are specific substances that couple with the sensing medium. In this case, both the sensing medium and the liquid sample are samples to be analyzed. As such a combination of specific substances and a sensing medium, there is, for example, a combination of an antigen and an antibody.

In the above-mentioned surface plasmon resonance sensor and leaky mode sensor, incidentally, the properties of a sample related to the refractive index thereof have been found based on values obtained by differentiating the photodetection signals output from the light-receiving elements of the photodetection means. Because of this, in the case of measuring an incidence angle $\theta_{sp}$ at which ATR takes place, for example, the width of a dark line corresponding to the incidence angle $\theta_{sp}$ is very narrow. When the width of the dark line is narrower than the pitch between two adjacent light-receiving elements of the photodetection means, a difference in the incidence angle $\theta_{sp}$, which corresponds to a difference in the position of incidence of a dark line whose width is less than the pitch between the light-receiving elements, cannot be detected and therefore an error in detection becomes great. In the case of measuring a change with the lapse of time in the incidence angle $\theta_{sp}$ at which ATR takes place, the change with lapse of time in the incidence angle $\theta_{sp}$ cannot be detected if a change in the incidence position of a dark line corresponding to the change with lapse of time in the incidence angle $\theta_{sp}$ is less than the pitch between the light-receiving elements. As a result, an error in detection becomes great and it becomes difficult to make an accurate analysis of a sample.

SUMMARY OF THE INVENTION

The present invention has been made in view of the circumstances mentioned above. Accordingly, it is the primary object of the present invention to provide a sensor, utilizing ATR, which is capable of adjusting the width of a dark line in a reflected light beam which corresponds to ATR, enhancing accuracy of detection, and making an accurate analysis of a sample.

To achieve this end and in accordance with an important aspect of the present invention, there is provided a sensor utilizing attenuated total reflection, comprising:

a dielectric block;

a thin film layer, formed on a surface of the dielectric block, for placing a sample thereon;

a light source for emitting a light beam;

an optical system for making the light beam enter the dielectric block at various angles of incidence so that a condition for total internal reflection is satisfied at an interface between the dielectric block and the thin film layer;

photodetection means, comprising a plurality of light-receiving elements juxtaposed in a predetermined direction and disposed to respectively receive components of the light beam satisfying the total internal reflection condition at the interface, for detecting the attenuated total reflection;

differentiation means for differentiating photodetection signals output from the light-receiving elements of the photodetection means, in the predetermined direction in which the light-receiving elements are juxtaposed; and adjustment means for optically expanding the width of a dark line, corresponding to the attenuated total reflection, of the light beam which falls on the photodetection means, so that the width of the dark line becomes greater than a pitch between the light-receiving elements.

In accordance with another important aspect of the present invention, there is provided a sensor utilizing attenuated total reflection, comprising:

a dielectric block;

a metal film, formed on a surface of the dielectric block, for placing a sample thereon;

a light source for emitting a light beam;

an optical system for making the light beam enter the dielectric block at various angles of incidence so that a condition for total internal reflection is satisfied at an interface between the dielectric block and the metal film;

photodetection means, comprising a plurality of light-receiving elements juxtaposed in a predetermined direction and disposed to respectively receive components of the light beam satisfying the total internal reflection condition at the interface, for detecting the attenuated total reflection caused by surface plasmon resonance;

differentiation means for differentiating photodetection signals output from the light-receiving elements of the photodetection means, in the predetermined direction in which the light-receiving elements are juxtaposed; and adjustment means for optically expanding the width of a dark line, corresponding to the attenuated total reflection, of the light beam which falls on the photodetection means, so that the width of the dark line becomes greater than a pitch between the light-receiving elements.

In accordance with still another important aspect of the present invention, there is provided a sensor utilizing attenuated total reflection, comprising:

a dielectric block;

a cladding layer formed on a surface of the dielectric block;

an optical waveguide layer, formed on a surface of the cladding layer, for placing a sample thereon;

a light source for emitting a light beam;

an optical system for making the light beam enter the dielectric block at various angles of incidence so that a condition for total internal reflection is satisfied at an interface between the dielectric block and the cladding layer;

photodetection means, comprising a plurality of light-receiving elements juxtaposed in a predetermined direction and disposed to respectively receive components of the light beam satisfying the total internal reflection condition at the interface, for detecting the attenuated total reflection caused by excitation of a waveguide mode in the optical waveguide layer;

differentiation means for differentiating photodetection signals output from the light-receiving elements of the photodetection means, in the predetermined direction in which the light-receiving elements are juxtaposed; and adjustment means for optically expanding the width of a dark line, corresponding to the attenuated total reflection, of the light beam which falls on the photodetection means, so that the width of the dark line becomes greater than a pitch between the light-receiving elements.

As described above, the three sensors according to the present invention is characterized by comprising the adjustment means for optically expanding the width of a dark line, corresponding to the attenuated total reflection, of the light beam which falls on the photodetection means, so that the width of the dark line becomes greater than a pitch between the light-receiving elements.

The width of the dark line refers to the width of a region where light intensity is reduced to more than half the difference between the minimum value of the light intensity in the dark line region and the light intensity in a region other than the dark line, when the components of the light beam are detected by the photodetection means. That is, the width of the dark line is equivalent to the reverse of the full width at half maximum intensity (FWHM).

The aforementioned sensors of the present invention may further comprise means for moving the adjustment means in and out of an optical path between the dielectric block and the photodetection means.

The aforementioned adjustment means can employ a diverging lens or diverging lens array. It can also employ a diffusing plate, a zoom lens, or the like.

The three sensors of the present invention may further comprise means for moving the photodetection means in the direction in which the light beam propagates.

In addition, the three sensors of the present invention may further comprise means for rotating the photodetection means on an axis substantially perpendicular to both the direction in which said light beam propagates and the predetermined direction in which the light-emitting elements are juxtaposed.

The differentiated value that is output from the aforementioned differentiation means, as it is, maybe displayed on display means and used for analyzing the properties of a sample. Based on the differentiated value, an incidence angle $\theta_{sp}$ at which ATR takes place may be automatically calculated and displayed on display means. In addition, every time a predetermined time elapses, a quantity of change in the differentiated value can be calculated from the differentiated value. Based on the quantity of change, the properties of a sample can be analyzed. Furthermore, based on the incidence angle $\theta_{sp}$, as well as a predetermined calibration curve, etc., a quantitative analysis of a specific substance in a sample may be automatically made and displayed on display means in real time.

It is preferable that the aforementioned differentiation means be capable of calculating a difference between photodetection signals output from adjacent light-receiving elements of the photodetection means. The photodetection means can suitably employ, for instance, a photodiode array, etc.

According to the present invention, the width of a dark line, corresponding to ATR, of the light beam which falls on the photodetection means, is optically expanded by the adjustment means so that the width of the dark line becomes greater than the pitch between the light-receiving elements. The dark line occurring in the light beam is received by two or more light-receiving elements. The light-receiving elements that are receiving the dark line will receive light having a light quantity which corresponds to the incidence angle $\theta_{sp}$ that is used for an analysis of the properties of a sample. Therefore, when differentiating the photodetection signals output from the light-receiving elements, in the direction in which the light-receiving elements are juxtaposed, and then detecting an incidence angle $\theta_{sp}$ or a change with the lapse of time in the angle from the differentiated value, the accuracy of detection is enhanced and therefore an analysis of a sample can be accurately made.

There are cases where the width of a dark line occurring in a light beam varies with sample types, the wavelength of the light beam, etc. If there is provided means for moving the adjustment means in and out of the optical path between the dielectric block and the photodetection means, the adjustment means can be disposed between dielectric block and the photodetection means when it is necessary to expand a light beam to widen the dark line. When there is no need to expand a light beam, a reduction in the quantity of the light beam due to the adjustment means can be prevented by moving the adjustment means out of the optical path between the dielectric block and the photodetection means.

If a diverging lens or diffusing plate is used as the adjustment means, an increase in the cost will be slight. In addition, if a zoom lens is employed as the adjustment means, a light beam can be expanded with a desired magnification ratio in accordance with the width of a dark line occurring in the light beam.

According to the present invention, there is provided means for moving the photodetection means in a direction in which a light beam propagates. Therefore, the width of a dark line corresponding to ATR can be adjusted by moving the photodetection means in the direction in which a light beam propagates, by the moving means. That is, when it is necessary to expand the width of the dark line, it becomes possible to make the width of the dark line greater than the pitch between the light-receiving elements by moving the photodetection means away from the dielectric block. Because of this, the dark line can be received by two or more light-receiving elements. Therefore, the light-receiving elements that are receiving the dark line can receive light which has a light quantity corresponding to an incident angle $\theta_{sp}$ that is used for an analysis of the properties of a sample.

Therefore, when differentiating the photodetection signals output from the light-receiving elements, in the direction in which the light-receiving elements are juxtaposed, and then detecting an incidence angle $\theta_{sp}$ or a change with the lapse of time in the angle from the differentiated value, the accuracy of detection is enhanced and therefore an analysis of a sample can be accurately made. Since there is no need to provide an optical component, such as a lens, a diffusing plate, etc., between the dielectric block and the photodetection means, a reduction in the light intensity due to an optical component can be prevented. In addition, a magnification ratio for the width of a dark line on the photodetection means can be set as desired.

According to the present invention, there is provided means for rotating the photodetection means on an axis substantially perpendicular to both the direction in which the light beam propagates and the predetermined direction in which the light-emitting elements are juxtaposed. Therefore, the width of a dark line corresponding to ATR can be adjusted by rotating the photodetection means by the rotation means. For example, when it is necessary to expand the width of the dark line, the photodetection means is rotated so that a light beam falls obliquely on the photodetection means. This makes it possible to make the width of the dark line greater than the pitch between the light-receiving elements of the photodetection means. Because of this, the dark line can be received by two or more light-receiving elements. Therefore, the light-receiving elements that are receiving the dark line can receive light which has a light quantity corresponding to an incident angle $\theta_{sp}$ that is used for an analysis of the properties of a sample. Thus, the section for measuring the light beam can be made structurally simple and compact. When differentiating the photodetection signals output from the light-receiving elements, in the direction in which the light-receiving elements are juxtaposed, and then detecting an incidence angle $\theta_{sp}$ or a change with the lapse of time in the angle from the differentiated value, the accuracy of detection is enhanced and therefore an analysis of a sample can be accurately made.

BRIEF DESCRIPTION OF THE DRAWINGS

The present invention will be described in further detail with reference to the accompanying drawings wherein:

FIG. 2 is a block diagram showing the electrical construction of the surface plasmon resonance sensor shown in FIG. 1;

FIG. 3A is a graph showing the relationship between the incidence angle of a light beam and the intensity of the light beam, obtained according to the surface plasmon resonance sensor shown in FIG. 1;

FIG. 3B is a diagram showing a photodiode array employed in the surface plasmon resonance sensor shown in FIG. 1;

FIG. 3C is a graph showing the relationship between the incidence angle of the light beam and the differentiated value of the output of photodetection means;

FIG. 6 is a side view showing a modification of a surface plasmon resonance sensor constructed according to a third embodiment of the present invention;

FIG. 7 is a side view showing a surface plasmon resonance sensor constructed according to a fourth embodiment of the present invention; and FIG. 8 is a side view showing a modification of the surface plasmon resonance sensor shown in FIG. 7.

DESCRIPTION OF THE PREFERRED EMBODIMENTS

Figure 1:
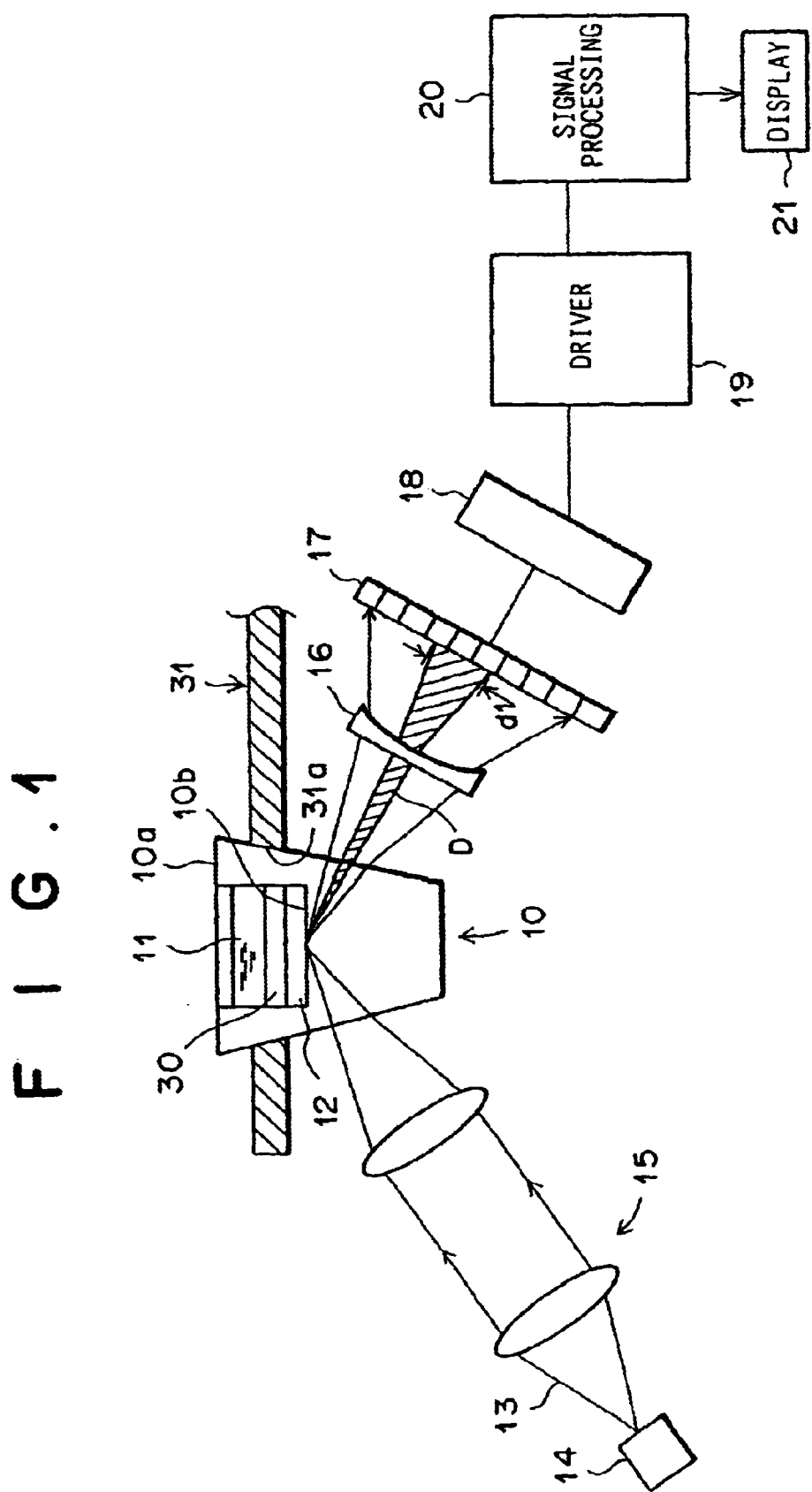
FIG. 1 is a side view showing a surface plasmon resonance sensor constructed according to a first embodiment of the present invention.
Figure 4:
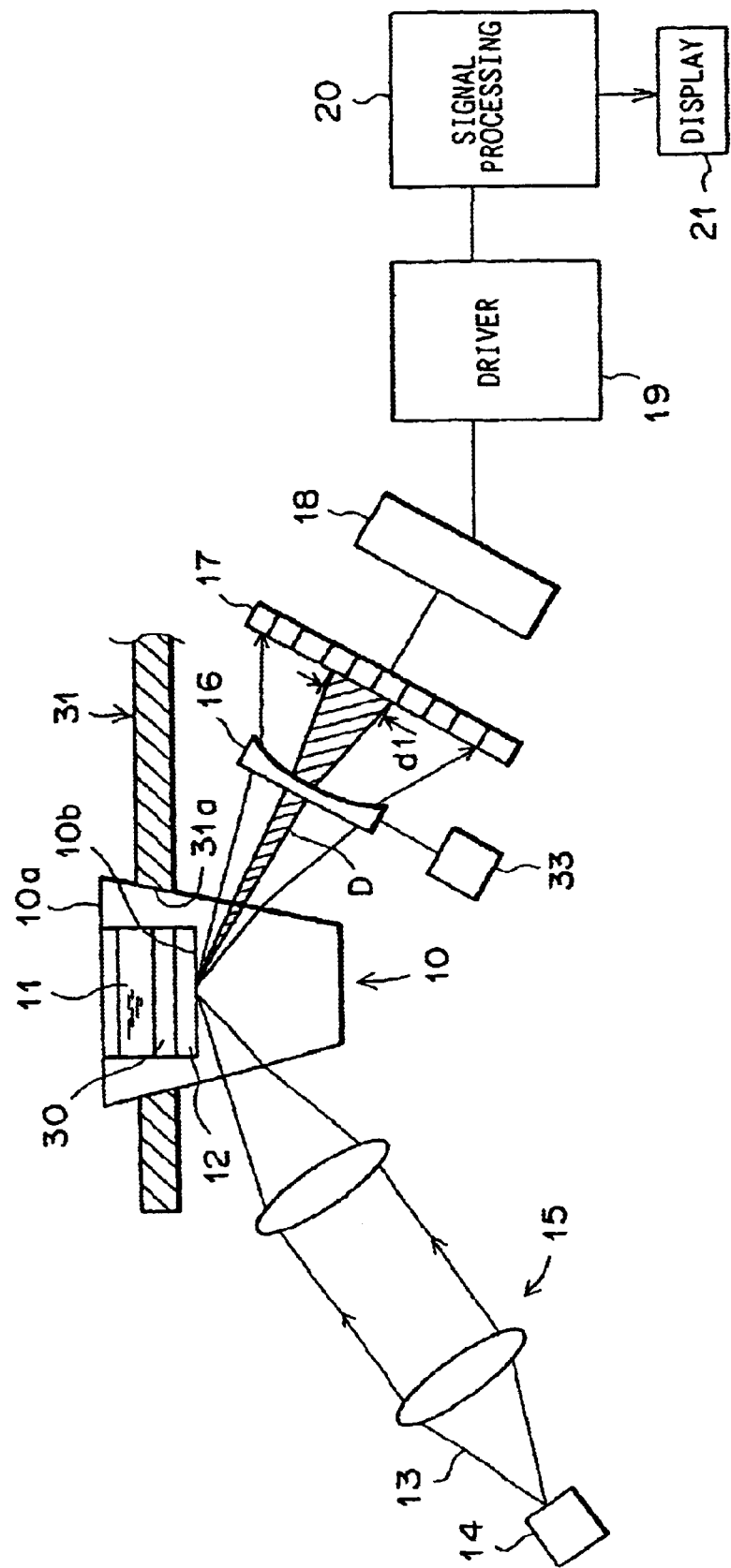
FIG. 4 is a side view showing a modification of the surface plasmon resonance sensor shown in FIG. 1.

Referring now in greater detail to the drawings and initially to FIG. 1, there is shown a surface plasmon resonance sensor in accordance with a first embodiment of the present invention. The surface plasmon resonance sensor has a dielectric block 10 and a metal film 12. The dielectric block 10 is formed, for example, into the shape of a generally quadrangular pyramid, a portion thereof being cut out. The metal film 12 is formed on a surface (top surface in FIG. 1) of the dielectric block 10, and is composed, for example, of gold, silver, copper, aluminum, etc.

The dielectric block 10 is formed, for example, from transparent resin, etc., and is thickened at a portion 10a thereof to form a sample holder portion in which a liquid sample 11 is stored. In the first embodiment, a sensing medium 30 (which is to be described later) is placed on the metal film 12.

The dielectric block 10 and the metal film 12 constitute a disposable measuring chip. A plurality of measuring chips are fitted in chip holding holes 31a formed in a turntable 31, respectively. With the dielectric blocks 10 thus fitted in the chip holding holes 31a of the turntable 31, the turntable 31 is intermittently rotated by a predetermined angle at a time. If a dielectric block 10 is stopped at a predetermined position, the liquid sample 11 is dropped into the dielectric block 10 and held within the sample holding portion 10a. If the turntable 31 is further rotated by a predetermined angle, the dielectric block 10 is moved to the measuring position shown in FIG. 1 and is stopped there.

The surface plasmon resonance sensor of the first embodiment, in addition to the dielectric block 10, is equipped with a light source 14, which consists of a semiconductor laser, etc., for emitting a light beam 13; an optical system 15 for making the light beam 13 enter the dielectric block 10 so that various angles of incidence are obtained with respect to an interface 10b between the dielectric block 10 and the metal film 12; and a concave lens or diverging lens 16 for diverging the beam diameter of the light beam 13 satisfying total internal reflection at the interface 10b. The surface plasmon resonance sensor is further equipped with photodetection means 17 for detecting the light beam 13 whose beam diameter has been expanded by the concave lens 16; a differential amplifier array 18 connected to the photodetection means 17; a driver 19; a signal processing section 20 constructed of a computer system, etc.; and display means 21 connected to the signal processing section 20.

FIG. 2 shows the electrical construction of the surface plasmon resonance sensor shown in FIG. 1. As shown in FIG. 2, the driver 19 is constructed of sample holding circuits 22a, 22b, 22c, . . . for holding outputs of the differential amplifiers 18a, 18b, 18c, . . . of the differential amplifier array 18; a multiplexer 23 to which outputs of the sample holding circuits 22a, 22b, 22c, . . . are input; and an A/D converter 24 for digitizing the output of the multiplexer 23 and then inputting the digitized output to the signal processing section 20. The driver 19 is further constructed of a drive circuit 25 for driving the multiplexer 23 and the sample holding circuits 22a, 22b, 22c, . . . ; and a controller 26 for controls operation of the drive circuit 25 in response to a control signal from the signal processing section 20.

As shown in FIG. 1, the light beam 13 emitted divergently from the laser light source 14 is converged on the interface 10b between the dielectric block 10 and the metal film 12 by the optical system 15. Thus, the light beam 13 contains components incident at various incidence angles θ with respect to the interface 10b. Note that the incidence angles θ are equal to or greater than a critical angle of incidence at which total internal reflection takes place. Hence, the light beam 13 is reflected at the interface 10b so that it satisfies total internal reflection. The reflected light beam 13 contains components reflected at various angles.

Note that the light beam 13 is p-polarized and then strikes the interface 10b. For this reason, the laser light source 14 needs to be disposed so that the polarization direction thereof becomes a predetermined direction. Alternatively, the direction of polarization of the light beam 13 may be controlled with a wavelength plate, a polarizing plate, etc.

The beam diameter of the light beam 13 satisfying total internal reflection at the interface 10b is expanded by the concave lens 16 and is detected by the photodetection means 17. The photodetection means 17 in the first embodiment is a photodiode array consisting of a plurality of photodiodes 17a, 17b, 17c, . . . juxtaposed in a row. As shown in FIG. 1, the direction in which the photodiodes are juxtaposed is substantially perpendicular to the traveling direction of the expanded light beam 13. Therefore, the components of the light beam 13 satisfying total internal reflection at various angles at the interface 10b are received by the different photodiodes 17a, 17b, 17c, . . . , respectively.

The outputs of the photodiodes 17a, 17b, 17c, . . . are input to the differential amplifiers 18a, 18b, 18c, . . . of the differential amplifier array 18. Note that the outputs of two adjacent photodiodes are input in common to a single differential amplifier. Therefore, the outputs of the differential amplifiers 18a, 18b, 18c, . . . are considered to be values obtained by differentiating the photodetection signals output from the photodiodes 17a, 17b, 17c, . . . , in the direction in which the photodiodes are juxtaposed.

The outputs of the differential amplifiers 18a, 18b, 18c, . . . are held at predetermined timings by the sample holding circuits 22a, 22b, 22c, . . . , respectively, and are input to the multiplexer 23. The multiplexer 23 inputs the held outputs of the differential amplifiers 18a, 18b, 18c, . . . to the A/D converter 24 in a predetermined order. The A/D converter 24 digitizes these outputs and then inputs the digitized signals to the signal processing section 20.

FIG. 3A shows the relationship between the incidence angle θ of the light beam 13 with respect to the interface 10b and the above-mentioned light intensity I. Light, incident at a specific angle $\theta_{sp}$ on the interface 10b between the metal film 12 and the sample 11, excites a surface plasmon at the interface 10b. Because of this, for the light incident at the specific angle $\theta_{sp}$, the intensity I of the reflected light drops sharply. That is, the specific incidence angle $\theta_{sp}$ is an angle of incidence at which ATR occurs. At the specific incidence angle $\theta_{sp}$, the reflected-light intensity I becomes the minimum value. The sharp drop in the reflected-light intensity I is observed as a dark line in the reflected light, as shown at D in FIG. 1.

FIG. 3B shows the direction in which the photodiodes 17a, 17b, 17c, . . . are juxtaposed. As described previously, the positions of the photodiodes 17a, 17b, 17c, . . . juxtaposed perpendicular to the reflected light correspond to the above-mentioned incidence angles θ. Because the beam diameter of the light beam 13 reflected at the interface 10b is expanded by the concave lens 16, the width d1 of the dark line D on the photodetection means 17 is about twice the pitch between the photodiodes of the photodetection means 17. The width d1 of the dark line D on the photodetection means 17 employs the width of a region where light intensity is reduced to more than half the difference between the minimum value of the light intensity in the dark line region and the light intensity in a region other than the dark line. That is, the width d1 employs a width equivalent to the reverse of the full width at half maximum intensity (FWHM).

FIG. 3C shows the relationship between the juxtaposed positions of the photodiodes 17a, 17b, 17c, . . . (i.e., the incidence angles θ) and the outputs I' of the differential amplifiers 18a, 18b, 18c, . . . (i.e., the differentiated values of the reflected-light intensities I).

Based on the differentiated value I' input from the A/D converter 24, the signal processing section 20 selects a differential amplifier (e.g., the differential amplifier 18e in FIG. 3) whose output is closest to a differentiated value I'=0 corresponding to the aforementioned incident angle $\theta_{sp}$, from among the differential amplifiers 18a, 18b, 18c, . . . Then, a differentiated value I' output from the selected differential amplifier is displayed on the display means 21. Note that there are cases where a differential amplifier outputting the differentiated value I'=0 is present. In that case, it is a matter of course that that differential amplifier is selected.

Thereafter, every time a predetermined time elapses, the differentiated value I' output from the selected differential amplifier 18e is displayed on the display means 21. If the dielectric constant or refractive index of the substance in contact with the metal film 12 (see FIG. 1) changes and therefore the curve in FIG. 3A is shifted in a horizontal direction, the differentiated value I' is increased or decreased according to the shift. Therefore, by continuously measuring the differentiated value I' with the lapse of time, a change in the refractive index of the substance in contact with the metal film 12, that is, a change in the property of the substance related to the refractive index, can be detected.

Particularly, in the first embodiment, the sensing medium 30 that couples with a specific substance in the liquid sample 11 is placed on the metal film 12, and according to the coupled state, the refractive index of the sensing medium 30 changes. Therefore, by continuously measuring the differentiated value I', how the coupled state changes can be detected. In this case, both the liquid sample 11 and the sensing medium are samples that are to be analyzed. As a combination of the specific substance and the sensing medium 30, there is, for instance, a combination of an antigen and an antibody.

As described above, the first embodiment employs the concave lens 16 to expand the beam diameter of the light beam 13. The width d1 of the dark line D in the light beam 13 on the photodetection means 17 is expanded to twice the interval of the photodiode of the photodetection means 17, as shown in FIG. 3A. The dark line D is received by 4 (four) photodiodes 17*d* to 17*g*. Because of this, if there is a change in the incidence angle $\theta_{sp}$ at which ATR takes place, the quantity of the light incident on the photodiodes 17*d* to 17*g* changes according to the angle change. Therefore, by measuring the difference between the photodetection signals detected by the photodiodes 17*e* and 17*f* selected from the four photodiodes, that is, a change with the lapse of time in the differentiated value between the two photodiodes, a change in the incidence angle $\theta_{sp}$ can be detected with a high degree of accuracy. As a result, an accurate analysis of a sample can be made.

The first embodiment also employs the photodetection means 17 consisting of a plurality of photodiodes 17*a*, 17*b*, 17*c*, . . . juxtaposed in a row. Therefore, even if the curve in FIG. 3A is greatly shifted in a horizontal direction according to a change in the liquid sample 11, it becomes possible to detect the darkline D accurately. That is, the use of the photodetection means 17 in the form of an array makes it possible to secure a large dynamic range of measurements.

Note that the differential amplifier array 18, consisting of differential amplifiers 18*a*, 18*b*, 18*c*, . . . , may be replaced with a single differential amplifier. In this case, the outputs of the photodiodes 17*a*, 17*b*, 17*c*, . . . are switched by a multiplexer so that two adjacent outputs are input in sequence to the single differential amplifier.

In addition, in order to observe the manner in which the coupled state between the specific substance in the liquid sample 11 and the sensing medium 30 changes with the lapse of time, the differentiated value I' maybe calculated and displayed, every time a predetermined time elapses. Furthermore, the difference ΔI' between the initial differentiated value I' (0) and the differentiated value I' (t) measured when a predetermined time elapses, may be calculated and displayed.

Note that as a modification of the first embodiment, the first embodiment may further be equipped with lens insertion means 33 for moving the concave lens 16 in and out of the optical path between the dielectric block 10 and the photodetection means 17. The lens insertion means 33 renders it possible to insert the concave lens 16 between dielectric block 10 and the photodetection means 17 when it is necessary to expand the light beam 13 to widen the dark line D. When there is no need to expand the light beam 13, a reduction in the quantity of the light beam 13 due to the concave lens 16 can be prevented by moving the concave 16 out of the optical path between the dielectric block 10 and the photodetection means 17. It is preferable that the width of the dark line D incident on the photodetection means 17 be within a range from about one time the photodiode pitch of the photodetection means 17 to about four times the photodiode pitch. Therefore, when the dark line D is sufficiently wide, it is preferable to move the concave lens 16 out of the optical path between the dielectric block 10 and the photodetection means 17.

Figure 5:
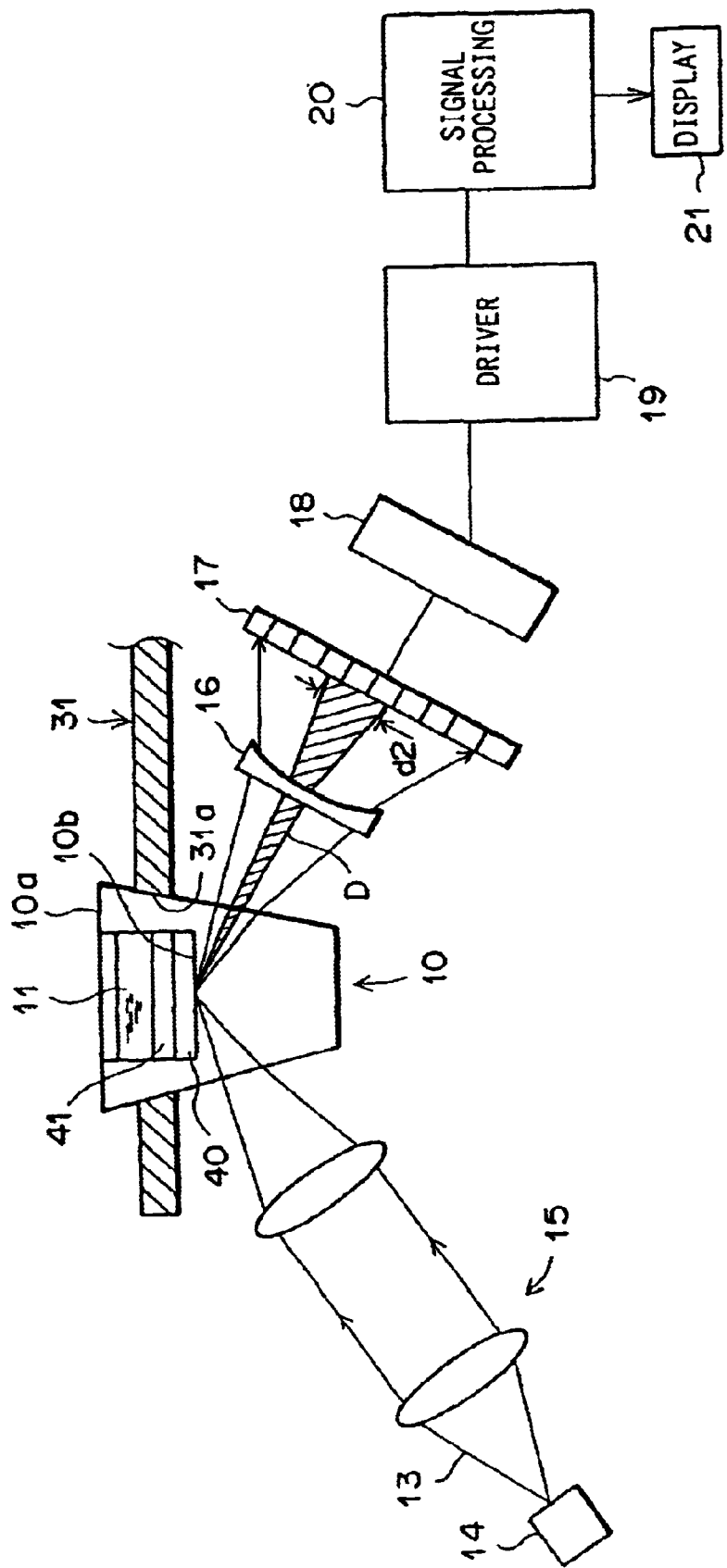
FIG. 5 is a side view showing a leaky mode sensor constructed according to a second embodiment of the present invention.

FIG. 5 shows a sensor constructed according to a second embodiment of the present invention. Note in the figure that the same reference numerals are applied to the same parts as those in FIG. 1, and that a description thereof will not be given unless particularly necessary.

The sensor of the second embodiment utilizing ATR is of the aforementioned leaky mode. As with the first embodiment, the second embodiment is constructed so that it employs a plurality of dielectric blocks 10 as measuring chips. Each dielectric block 10 has a cladding layer 40 on a surface thereof (e.g., the top surface in FIG. 5), and an optical waveguide layer 41 is formed on the cladding layer 40.

The dielectric block 10 is formed, for example, from synthetic resin, or optical glass such as BK7, etc. The cladding layer 40 is formed into the shape of a thin film from a dielectric lower in refractive index than the dielectric block 10, or metal such as gold, etc. The optical waveguide layer 41 is also formed into the shape of a thin film from a dielectric higher in refractive index than the cladding layer 40, such as polymethylmethacrylate (PMMA). The cladding layer 40 is 36.5 nm in thickness when it is formed from a thin gold film. The optical waveguide layer 41 is about 700 nm in thickness when it is formed from PMMA.

In the leaky mode sensor of the third embodiment, if a light beam 13 emitted from a laser light 14 strikes the cladding layer 40 through the dielectric block 10 at incidence angles equal to or greater than an angle at which total internal reflection occurs, the light beam 13 satisfies total internal reflection at an interface 10*b* between the dielectric block 10 and the cladding layer 40. However, light with a specific wave number, incident on the optical waveguide layer 41 through the cladding layer 40 at a specific incidence angle, propagates in the optical waveguide layer 41 in a waveguide mode. If the waveguide mode is thus excited, the greater part of the incident light is confined within the optical waveguide layer 41, and consequently, ATR occurs in which the intensity of light satisfying total internal reflection at the interface 10*b* drops sharply.

Since the wave number of light propagating in the optical waveguide layer 41 depends on the refractive index of the sample 11 on the optical waveguide layer 41, the refractive index of the sample 11 and/or the properties of the sample 11 related to the refractive index can be analyzed by finding the above-mentioned specific incidence angle at which ATR occurs. In addition, the properties of the sample 11 can be analyzed based on the reflected-light intensity I near the above-mentioned specific incidence angle, or the differentiated value I' output from each differential amplifier of a differential amplifier array 18.

In the second embodiment, as with the first embodiment, the beam diameter of the light beam 13 is expanded by the concave lens 16, and the expanded light beam 13 falls on the photodetection means 17. Therefore, as with the first embodiment, the width d2 of the dark line D incident on the photodetection means 17 is about twice the pitch between the photodiodes of the photodetection means 17. The dark line D is received by two or more photodiodes. An accurate analysis of the sample 11 can be made by measuring the difference between the photodetection signals output from photodiodes suitably selected from the two or more photodiodes, that is, a change with the lapse of time in a differentiated value between photodiodes. Note that as with the first embodiment, the second embodiment may further comprise lens insertion means for moving the concave lens 16 in and out of the optical path between the dielectric block 10 and the photodetection means 17.

FIG. 6 shows a sensor constructed according to a third embodiment of the present invention. Note in the figure that the same reference numerals are applied to the same parts as those in FIG. 1, and that a description thereof will not be given unless particularly necessary.

The sensor of the third embodiment utilizing ATR is the aforementioned surface plasmon resonance sensor. As with the first embodiment, the third embodiment is constructed so that it employs a plurality of dielectric blocks 10 as measuring chips.

In the surface plasmon resonance sensor of the third embodiment, a diffusing plate 50 for diffusing a light beam satisfying at an interface 10a is disposed between the dielectric block 10 and photodetection means 17. The photodetection means 17 is used to detect the light intensity of the light beam 13 diffused by the diffusing plate 50.

As illustrated in FIG. 6, the light beam 13 emitted divergently from a laser light source 14 converges on the interface 10b between the dielectric block 10 and the metal film 12 by operation of an optical system 15. The light beam 13 satisfying total internal reflection at the interface 10b is diffused by the diffusing plate 50 and is detected by the photodetection means 17. Note that the light beam 13 reflected at the interface 10b is diffused so that the width d3 of a dark line D incident on the photodetection means 17 is about twice the pitch between the photodiodes of the photodetection means 17.

The components of the light beam 13 satisfying total internal reflection at various angles of reflection at the interface 10b are received by the different photodiodes 17a, 17b, 17c, . . . , respectively. As with the first embodiment, the outputs of the photodiodes 17a, 17b, 17c, . . . are input to the differential amplifiers 18a, 18b, 18c, . . . of a differential amplifier array 18, respectively. The outputs of the differential amplifiers 18a, 18b, 18c, . . . are held at predetermined timings by sample holding circuits 22a, 22b, 22c, . . . , and are input to a multiplexer 23. The multiplexer 23 inputs the held outputs of the differential amplifiers 18a, 18b, 18c, . . . to an A/D converter 24 in a predetermined order. The A/D converter 24 digitizes these outputs and then inputs the digitized signals to a signal processing section 20.

In the third embodiment, as with the first embodiment, the beam diameter of the light beam 13 is expanded by the diffusing plate 50, and the expanded light beam 13 falls on the photodetection means 17. Therefore, as with the first embodiment, the width d3 of the dark line D incident on the photodetection means 17 is about twice the photodiode pitch. The dark line D is received by two or more photodiodes. Thus, an accurate analysis of the sample 11 can be made by measuring the difference between the photodetection signals output from photodiodes selected suitably from the two or more photodiodes, that is, a change with the lapse of time in a differentiated value between photodiodes. Note that as a modification of the third embodiment, the concave lens 16 of the leaky mode sensor shown in FIG. 5 can be replaced with the diffusing plate 50. The diffusing plate 50 may be equipped with plate insertion means for moving the diffusing plate 50 in and out of the optical path between the electric block 19 and the photodetection means 17. As another modification of the third embodiment, the diffusing plate 50 may be replaced with a zoom lens. In this case, the light beam 13 can be expanded with a desired magnification ratio so that a desired width of the dark line D is obtained.

FIG. 7 shows a sensor constructed according to a fourth embodiment of the present invention. Note in the figure that the same reference numerals are applied to the same parts as those in FIG. 1, and that a description thereof will not be given unless particularly necessary.

The sensor of the fourth embodiment utilizing ATR is the aforementioned surface plasmon resonance sensor. As with the first embodiment, the fourth embodiment is constructed so that it employs a plurality of dielectric blocks 10 as measuring chips.

The surface plasmon resonance sensor of the fourth embodiment is equipped with means 60 for moving photodetection means 17 along the traveling direction of a light beam 13. As illustrated in FIG. 7, the light beam 13 emitted divergently from a laser light source 14 converges on the interface 10b between the dielectric block 10 and the metal film 12 by operation of an optical system 15. The light beam 13 satisfying total internal reflection at the interface 10b is detected by the photodetection means 17. When the width of a dark line D is narrow, the photodetection means 17 is moved to a solid-line position in FIG. 7 by the moving means 60. Since the distance from the interface 10b to the photodetection means 17 becomes longer and the light beam 13 incident on the photodetection means 17 is expanded, the width d4 of the dark line D on the photodetection means 17 is increased to about twice the photodiode pitch.

The components of the light beam 13 satisfying total internal reflection at various angles of reflection at the interface 10b are received by the different photodiodes 17a, 17b, 17c, . . . , respectively. As with the first embodiment, the outputs of the photodiodes 17a, 17b, 17c, . . . are input to the differential amplifiers 18a, 18b, 18c, . . . of a differential amplifier array 18, respectively. The outputs of the differential amplifiers 18a, 18b, 18c, . . . are held at predetermined timings by sample holding circuits 22a, 22b, 22c, . . . , and are input to a multiplexer 23. The multiplexer 23 inputs the held outputs of the differential amplifiers 18a, 18b, 18c, . . . to an A/D converter 24 in a predetermined order. The A/D converter 24 digitizes these outputs and then inputs the digitized signals to a signal processing section 20.

In the fourth embodiment, the width d4 of the dark line D can be expanded to two or more times the photodiode pitch without inserting an optical component, such as a lens, a diffusing plate, etc., between the dielectric 10 and the photodetection means 17. Therefore, an accurate analysis of the sample 11 can be made by measuring the difference between the photodetection signals output from photodiodes selected suitably from the photodiodes on which the dark line is incident, that is, by measuring a change with the lapse of time in a differentiated value between photodiodes. In addition, there is no reduction in the light intensity due to a lens, a diffusing plate, etc., and the width d4 of the dark line D can be adjusted to a desired width.

As a modification of the fourth embodiment, the moving means 60 may be replaced with rotation means 61. As shown in FIG. 8, the rotation means 61 is used to rotate the photodetection means 17 on an axis substantially perpendicular to both the propagating direction of the light beam and the juxtaposed direction of the photodiodes. When the width of the dark line D is narrow, the photodetection means 17 is rotated from the dotted line position in FIG. 8 to the solid-line position by the rotation means 61. Because the light beam 13 falls obliquely on the photodetection means 17 and therefore the light beam 13 incident on the photodetection means 17 is expanded, the width d5 of the dark line D is also expanded to two or more times the photodiode pitch. In addition, the width d5 of the dark line D incident on the photodetection means 17 can be adjusted to a desired width by controlling the angle of rotation of the photodetection means 17. Besides, the measuring section for the light beam 13 can be made compact. Furthermore, if the moving means 60 and the rotational means 61 are combined together, the photodetection means 17 can be moved obliquely.

As another modification of the fourth embodiment, the aforementioned leaky mode sensor may be provided with the moving means 60, or the rotation means 61, or a combination of them.

In the aforementioned embodiments, the width of the dark line D on the photodetection means 17 is two or more times the pitch between the photodiodes of the photodetection means 17. However, if the width of the dark line D is one or more times the photodiode pitch, similar advantages can be obtained. In addition, if the dark line D is too wide, the differentiated value will be near 0. Therefore, it is preferable that the width of the dark line D be equal to or less than 4 times the photodiode pitch.

Although the present invention has been described with a certain degree of particularity, it is understood that the present disclosure has been made only by way of example and that numerous changes in the details of the construction and the combination and arrangement of parts may be made within the scope of the invention hereinafter claimed.

What is claimed is:

1. A sensor utilizing attenuated total reflection, comprising:
    a dielectric block;
    a thin film layer, formed on a surface of said dielectric block, for placing a sample thereon;
    a light source for emitting a light beam;
    an optical system for making said light beam enter said dielectric block at various angles of incidence so that a condition for total internal reflection is satisfied at an interface between said dielectric block and said thin film layer;
    photodetection means, comprising a plurality of light-receiving elements juxtaposed in a predetermined direction and disposed to respectively receive components of said light beam satisfying said total internal reflection condition at said interface, for detecting said attenuated total reflection;
    differentiation means for differentiating photodetection signals output from the light-receiving elements of said photodetection means, in said predetermined direction in which said light-receiving elements are juxtaposed; and
    adjustment means for optically expanding the width of a dark line, corresponding to said attenuated total reflection, of said light beam which falls on said photodetection means, so that the width of said dark line becomes greater than a pitch between said light-receiving elements.

2. A sensor utilizing attenuated total reflection, comprising:
    a dielectric block;
    metal film, formed on a surface of said dielectric block, for placing a sample thereon;
    a light source for emitting a light beam;
    an optical system for making said light beam enter said dielectric block at various angles of incidence so that a condition for total internal reflection is satisfied at an interface between said dielectric block and said metal film;
    photodetection means, comprising a plurality of light-receiving elements juxtaposed in a predetermined direction and disposed to respectively receive components of said light beam satisfying said total internal reflection condition at said interface, for detecting said attenuated total reflection caused by surface plasmon resonance;
    differentiation means for differentiating photodetection signals output from said light-receiving elements of said photodetection means, in said predetermined direction in which said light-receiving elements are juxtaposed; and
    adjustment means for optically expanding the width of a dark line, corresponding to said attenuated total reflection, of said light beam which falls on said photodetection means, so that the width of said dark line becomes greater than a pitch between said light-receiving elements.

3. A sensor utilizing attenuated total reflection, comprising:
    a dielectric block;
    a cladding layer formed on a surface of said dielectric block;
    an optical waveguide layer, formed on a surface of said cladding layer, for placing a sample thereon;
    a light source for emitting a light beam;
    an optical system for making said light beam enter said dielectric block at various angles of incidence so that a condition for total internal reflection is satisfied at an interface between said dielectric block and said cladding layer;
    photodetection means, comprising a plurality of light-receiving elements juxtaposed in a predetermined direction and disposed to respectively receive components of said light beam satisfying said total internal reflection condition at said interface, for detecting said attenuated total reflection caused by excitation of a waveguide mode in said optical waveguide layer;
    differentiation means for differentiating photodetection signals output from said light-receiving elements of said photodetection means, in said predetermined direction in which said light-receiving elements are juxtaposed; and
    adjustment means for optically expanding the width of a dark line, corresponding to said attenuated total reflection, of said light beam which falls on said photodetection means, so that the width of said dark line becomes greater than a pitch between said light-receiving elements.

4. The sensor as set forth in claim 1, further comprising means for moving said adjustment means in and out of an optical path between said dielectric block and said photodetection means.

5. The sensor as set forth in claim 2, further comprising means for moving said adjustment means in and out of an optical path between said dielectric block and said photodetection means.

6. The sensor as set forth in claim 3, further comprising means for moving said adjustment means in and out of an optical path between said dielectric block and said photodetection means.

7. The sensor as set forth in claim 1, wherein said adjustment means is a diverging lens.

8. The sensor as set forth in claim 2, wherein said adjustment means is a diverging lens.

9. The sensor as set forth in claim 3, wherein said adjustment means is a diverging lens.

10. The sensor as set forth in claim 1, wherein said adjustment means is a diffusing plate.

11. The sensor as set forth in claim 2, wherein said adjustment means is a diffusing plate.

12. The sensor as set forth in claim 3, wherein said adjustment means is a diffusing plate.

13. The sensor as set forth in claim 1, wherein said adjustment means is a zoom lens.

14. The sensor as set forth in claim 2, wherein said adjustment means is a zoom lens.

15. The sensor as set forth in claim 3, wherein said adjustment means is a zoom lens.

16. A sensor utilizing attenuated total reflection, comprising:

a dielectric block;

a thin film layer, formed on a surface of said dielectric block, for placing a sample thereon;

a light source for emitting a light beam;

an optical system for making said light beam enter said dielectric block at various angles of incidence so that a condition for total internal reflection is satisfied at an interface between said dielectric block and said thin film layer;

photodetection means, comprising a plurality of light-receiving elements juxtaposed in a predetermined direction and disposed to respectively receive components of said light beam satisfying said total internal reflection condition at said interface, for detecting said attenuated total reflection;

differentiation means for differentiating photodetection signals output from the light-receiving elements of said photodetection means, in said predetermined direction in which said light-receiving elements are juxtaposed; and means for moving said photodetection means in a direction in which said light beam propagates to adjust a width of said light beam incident on said photodetection means.

17. A sensor utilizing attenuated total reflection, comprising:

a dielectric block;

a metal film, formed on a surface of said dielectric block, for placing a sample thereon;

a light source for emitting a light beam;

an optical system for making said light beam enter said dielectric block at various angles of incidence so that a condition for total internal reflection is satisfied at an interface between said dielectric block and said metal film;

photodetection means, comprising a plurality of light-receiving elements juxtaposed in a predetermined direction and disposed to respectively receive components of said light beam satisfying said total internal reflection condition at said interface, for detecting said attenuated total reflection caused by surface plasmon resonance;

differentiation means for differentiating photodetection signals output from said light-receiving elements of said photodetection means, in said predetermined direction in which said light-receiving elements are juxtaposed; and means for moving said photodetection means in a direction in which said light beam propagates to adjust a width of said light beam incident on said photodetection means.

18. A sensor utilizing attenuated total reflection, comprising:

a dielectric block;

a cladding layer formed on a surface of said dielectric block;

an optical waveguide layer, formed on a surface of said cladding layer, for placing a sample thereon; a light source for emitting a light beam;

an optical system for making said light beam enter said dielectric block at various angles of incidence so that a condition for total internal reflection is satisfied at an interface between said dielectric block and said cladding layer;

photodetection means, comprising a plurality of light-receiving elements juxtaposed in a predetermined direction and disposed to respectively receive components of said light beam satisfying said total internal reflection condition at said interface, for detecting said attenuated total reflection caused by excitation of a waveguide mode in said optical waveguide layer;

differentiation means for differentiating photodetection signals output from said light-receiving elements of said photodetection means, in said predetermined direction in which said light-receiving elements are juxtaposed; and means for moving said photodetection means in a direction in which said light beam propagates to adjust a width of said light beam incident on said photodetection means.

19. A sensor utilizing attenuated total reflection, comprising:

a dielectric block;

a thin film layer, formed on a surface of said dielectric block, for placing a sample thereon;

a light source for emitting a light beam;

an optical system for making said light beam enter said dielectric block at various angles of incidence so that a condition for total internal reflection is satisfied at an interface between said dielectric block and said thin film layer;

photodetection means, comprising a plurality of light-receiving elements juxtaposed in a predetermined direction and disposed to respectively receive components of said light beam satisfying said total internal reflection condition at said interface, for detecting said attenuated total reflection;

differentiation means for differentiating photodetection signals output from the light-receiving elements of said photodetection means, in said predetermined direction in which said light-receiving elements are juxtaposed; and means for rotating said photodetection means on an axis approximately perpendicular to both a direction in which said light beam propagates and said predetermined direction in which said light-emitting elements are juxtaposed.

20. A sensor utilizing attenuated total reflection, comprising:

a dielectric block;

a metal film, formed on a surface of said dielectric block, for placing a sample thereon;

a light source for emitting a light beam;

an optical system for making said light beam enter said dielectric block at various angles of incidence so that a condition for total internal reflection is satisfied at an interface between said dielectric block and said metal film;

photodetection means, comprising a plurality of light-receiving elements juxtaposed in a predetermined direction and disposed to respectively receive components of said light beam satisfying said total internal reflection condition at said interface, for detecting said attenuated total reflection caused by surface plasmon resonance;

differentiation means for differentiating photodetection signals output from said light-receiving elements of said photodetection means, in said predetermined direction in which said light-receiving elements are juxtaposed; and means for rotating said photodetection means on an axis approximately perpendicular to both a direction in which said light beam propagates and said predetermined direction in which said light-emitting elements are juxtaposed.

21. A sensor utilizing attenuated total reflection, comprising:

a dielectric block;

a cladding layer formed on a surface of said dielectric block;

an optical waveguide layer, formed on a surface of said cladding layer, for placing a sample thereon;

a light source for emitting a light beam;

an optical system for making said light beam enter said dielectric block at various angles of incidence so that a condition for total internal reflection is satisfied at an interface between said dielectric block and said cladding layer;

photodetection means, comprising a plurality of light-receiving elements juxtaposed in a predetermined direction and disposed to respectively receive components of said light beam satisfying said total internal reflection condition at said interface, for detecting said attenuated total reflection caused by excitation of a waveguide mode in said optical waveguide layer;

differentiation means for differentiating photodetection signals output from said light-receiving elements of said photodetection means, in said predetermined direction in which said light-receiving elements are juxtaposed; and means for rotating said photodetection means on an axis approximately perpendicular to both a direction in which said light beam propagates and said predetermined direction in which said light-emitting elements are juxtaposed.

22. The sensor as set forth in any one of claims 1 through 3, wherein said differentiation means calculates a difference between photodetection signals output from two adjacent light-emitting elements of said photodetection means.

23. The sensor as set forth in any one of claims 1 through 3, wherein said photodetection means is a photodiode array.

* * * * *